(12) United States Patent
Suddath et al.

(10) Patent No.: US 6,821,480 B2
(45) Date of Patent: Nov. 23, 2004

(54) WATER LINE DECONTAMINATION SYSTEM

(76) Inventors: James N. Suddath, 5593 Northcote, West Bloomfield, MI (US) 48322; William Piskorowski, 11775 Hiawatha, Shelby Township, MI (US) 48315; Jerome J. Kasbrick, 5270 Eastbrook, Shelby Township, MI (US) 48316

(*) Notice: Subject to any disclaimer, the term of this patent is extended or adjusted under 35 U.S.C. 154(b) by 206 days.

(21) Appl. No.: 10/052,048

(22) Filed: Jan. 17, 2002

(65) Prior Publication Data
US 2002/0102182 A1 Aug. 1, 2002

Related U.S. Application Data
(60) Provisional application No. 60/265,060, filed on Jan. 30, 2001.

(51) Int. Cl.[7] .................................. A61L 2/00
(52) U.S. Cl. ................ 422/26; 392/485; 422/292; 422/293; 422/295; 422/297; 433/32
(58) Field of Search ................ 138/8; 392/485; 433/32; 422/26, 292, 297, 293, 295

(56) References Cited

U.S. PATENT DOCUMENTS

| | | | | |
|---|---|---|---|---|
| 3,980,131 A | * | 9/1976 | Perle et al. | 165/61 |
| 6,212,333 B1 | * | 4/2001 | Olk et al. | 392/485 |
| 6,454,871 B1 | * | 9/2002 | Labib et al. | 134/8 |

* cited by examiner

Primary Examiner—Krisanne Jastrzab
(74) Attorney, Agent, or Firm—Gifford, Krass, Groh, Sprinkle, Anderson & Citkowski, P.C.

(57) ABSTRACT

A self-cleaning system for delivering sanitized water to a workstation has a boiler which produces heat-sanitized water and steam. A diverter valve permits a fluid delivery line of the system to convey either sanitized water or steam to a workstation. The steam serves to sanitize the delivery line and workstation and removes biofilms therefrom.

21 Claims, 4 Drawing Sheets

WATER LINE DECONTAMINATION SYSTEM

RELATED APPLICATION

This application claims priority of U.S. Provisional Patent Application 60/265,060 filed Jan. 30, 2001 which is incorporated herein by reference.

FIELD OF THE INVENTION

This invention relates generally to systems and methods for delivering sanitized water and for decontaminating fluid delivery lines. More specifically, the invention relates to a system and method for providing a self-cleaning fluid delivery system. In specific embodiments, the invention is directed to a self-cleaning dental drilling and irrigation system.

BACKGROUND OF THE INVENTION

The formation of microbial biofilm is a significant problem in fluid delivery systems, particularly those used in dental, medical and food service applications, and various governmental and professional organizations are implementing standards and regulations for addressing this problem. Biofilm buildup occurs when bacteria or other microbes colonize tubing walls of fluid delivery systems. The biofilm forms a slime layer which fosters and protects growing microbes and hinders their removal and treatment. Generally, fluid flow in most delivery systems is laminar, and this favors the build up of biofilm. Biofilm represents a reservoir of contamination, and can support the growth of secondary organisms such as fungi, protozoa and nematodes. Biofilm can dislodge in the course of use of the system, and can present a significant source of infection.

Biofilm build up is of particular concern in medical and dental applications. The problem is compounded because medical and dental fluid delivery systems are frequently highly complex, expensive and thus difficult to clean or replace. Heretofore, biofilm control was attempted by flushing fluid delivery systems with biocidal compositions. This approach has been found to be ineffective. As noted above, fluid flow through such systems is generally laminar; hence, a flowing biocide does not effectively interact with biofilms. These problems are compounded because of the smooth, adherent nature of most biofilms. In fact, such cleaning attempts have been found to encourage the growth of biocide resistant organisms within the biofilm. Highly aggressive cleaning compositions such as alkalis, acids or the like generally cannot be used in complex medical and dental fluid delivery systems, since such aggressive chemicals can damage sensitive components of the systems; furthermore, residues from such aggressive chemicals can present a hazard to patients. In view of the general ineffectiveness of such chemical treatment methods, the only other approach heretofore available was to disassemble and manually clean and/or replace components of the system. This approach is clearly very expensive and time consuming. Furthermore, new biofilm buildup occurs fairly rapidly.

U.S. Pat. No. 5,556,279 discloses a system which employs iodine for purifying water supplied to a dental unit. The purified water limits the activity of microorganisms; however, it cannot completely stop biofilm buildup and does not function to remove biofilms which are already in place. Another approach to the problem of biofilms in dental systems is disclosed in U.S. Pat. No. 6,212,333. The system disclosed therein employs heat to sanitize incoming water. This sanitized water is then delivered by a pump to a dental workstation. Again, while the system of the '333 patent does sanitize water, this sanitized water is ineffective against biofilms already in the dental unit. Also, even though the water is heat sanitized, there is typically some residual biological activity which can initiate or contribute to biofilm growth.

Clearly, there is a need for a system and method which can provide sanitized water to a dental unit or other such workstation, and which can further function to remove biofilm buildup therefrom. Ideally, biofilm removal should not require any disassembly of the fluid delivery system and should be accomplished without the use of corrosive or otherwise dangerous chemicals. As will be explained hereinbelow, the present invention comprises a system which is operable to provide sanitized water to a fluid delivery system and which is further operable to destroy and remove biofilms from that system. The sanitization process of the present invention is accomplished through the use of steam. The sanitization process of the present invention does not require disassembly of the equipment being sanitized, and hence is very useful for cleaning fluid delivery systems associated with dental and medical equipment such as drill motors, dialysis units and the like. The system of the present invention is simple in design and low in cost and can be incorporated into specific workstations or equipment.

It is to be understood that while the system of the present invention is described and discussed herein with regard to dental and medical equipment, the benefits and advantages of the present invention will make it readily adaptable to all systems which require the delivery of sanitized fluid, and which are prone to biofilm buildup. As such, the present invention finds utility in connection with water coolers, beverage vending machines, soft drink and beer delivery systems, bottling systems and other food processing and delivery equipment. Biofilm buildup is also of concern in various industrial processes wherein microbial contamination can contaminate products or interfere with processing, and the present invention may be readily incorporated thereinto. In view of the teaching presented herein, it is to be understood that this invention may be employed in any application wherein there is a need to control and/or remove biofilm buildup in fluid systems. These and other advantages of the invention will be apparent from the drawings, discussion and description which follow.

BRIEF DESCRIPTION OF THE INVENTION

There is disclosed herein a self-cleaning system for delivering sanitized water to a workstation, such as a dental unit. The system includes a boiler which is connectable to a source of water by a water inlet and which is operable to provide steam and heat sanitized water. The system may optionally include a sanitized water reservoir which is integral with, or in fluid communication with, the boiler. The system further includes a sanitized water delivery line and a steam delivery line in fluid communication with the boiler, as well as a fluid delivery line. A diverter valve is in fluid communication with the sanitized water delivery line, the steam delivery line and the fluid delivery line, and is operable to selectively establish fluid communication between the fluid delivery line and either the steam delivery line or the sanitized water delivery line. In this manner, either sanitized water or steam may be delivered to the fluid delivery line. When steam is supplied to the line, this steam will function to destroy and remove biofilm contamination.

In further embodiments of the present invention, a heat exchanger is disposed so as to cool the heat sanitized water coming from the boiler. The excess heat removed by the heat exchanger may be used to warm input water to the boiler and/or to heat a stream of air. In specific embodiments, the boiler operates at a pressure above atmospheric, typically 1.5 to 2.0 atmospheres, and the steam pressure generated thereby may be employed to move the sanitized water through the system without the aid of a pump.

The system of the present invention may further include water softeners, filters or other conditioners associated with the water input line. In certain embodiments, the system may be further adapted to selectably introduce a biocidal composition into the fluid delivery line, and this biocide may be used in conjunction with the steam to aid in cleaning and sanitizing the fluid delivery system.

DETAILED DESCRIPTION OF THE INVENTION

The present invention will be described with reference to specific embodiments of water purification and water line decontamination systems adapted for use in a dental office. It is to be understood that other embodiments of the present invention may be utilized in other applications.

The system of the present invention operates to deliver sanitized water to a workstation, which may be a dental workstation, a beverage dispenser or other food service apparatus, medical equipment, industrial equipment or the like. Within the context of this disclosure, sanitized water is generally understood to be water which is sterilized or which has a very low concentration of microbes therein. In general, water having no more than 200 colony forming units per milliliter (200 CFU/ML) is recognized in the art as being sanitized water.

The system of the present invention is configured to receive water from a conventional source such as a water main, bottled water or the like. The water is sanitized by heat generated by a boiler. The boiler is also operative to generate steam. The sanitized water is conveyed via a delivery line to a workpiece unit such as a dental drill, a dental irrigator or the like. The system of the present invention is configured to include one or more diverter valves which permit steam, as generated by the boiler, to be routed through the water delivery lines. The system can also be adapted to deliver the steam to compressed air lines or other structures. This live steam has been found to be highly effective in removing biofilm and destroying other sources of biocontamination in the delivery system. The system of the present invention is relatively compact and low in cost; and hence can be installed at each dental workstation, or in other such equipment. The system can be activated to sterilize dental irrigators, drill handpieces and the like prior to the treatment of each patient.

Figure 1:
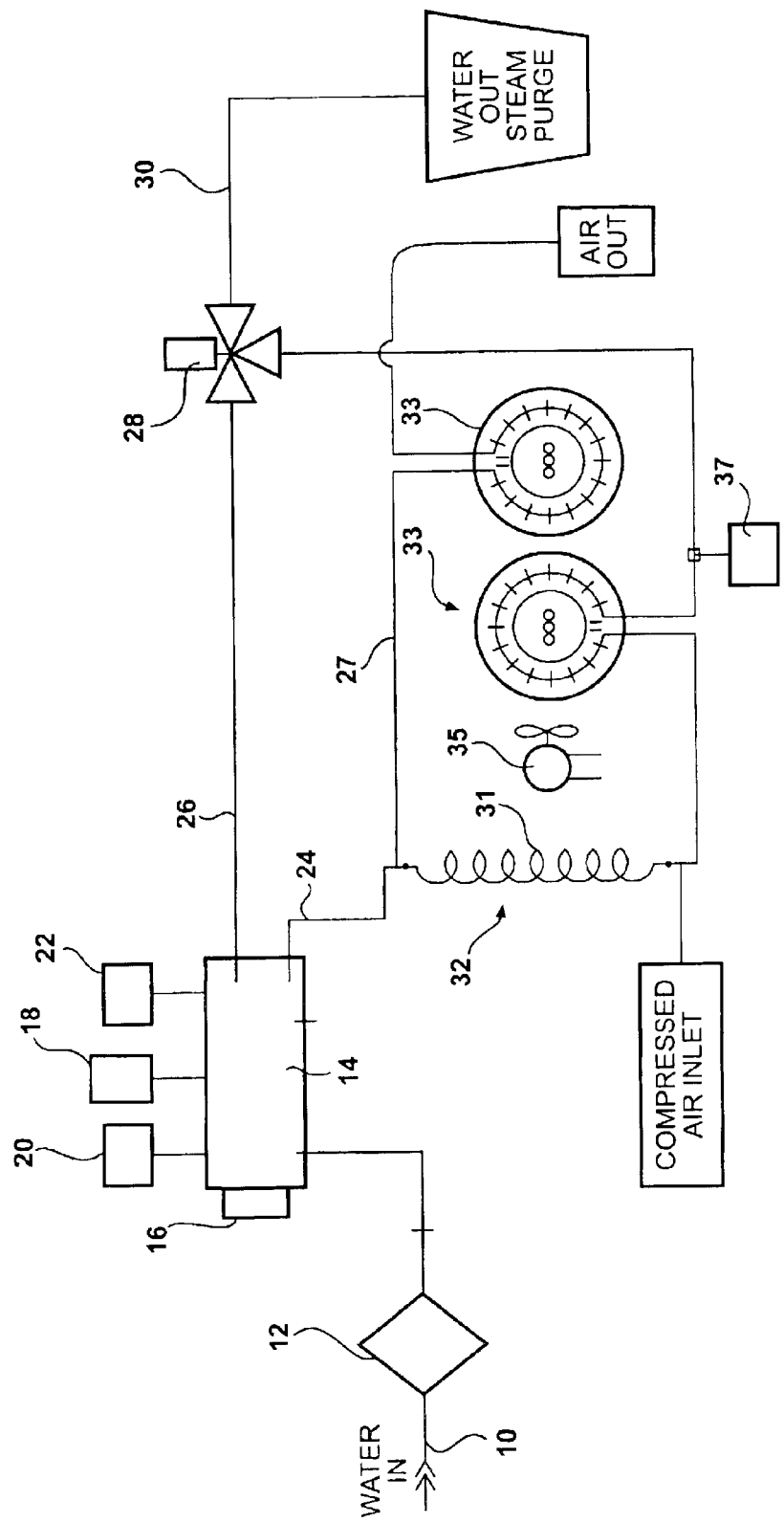
FIG. 1 is a schematic view of one embodiment of water line system in accord with the present invention.

FIG. 1 is a schematic depiction of one system of the type described hereinabove. As will be seen from the figure, the system includes a water inlet line 10, which may optionally include a water softener unit. The input water is conveyed to a boiler unit 14 where it is heated by a heater 16. Heating of the water generates steam, and the system is operated so as to assure that heating is carried out at a combination of time and temperature sufficient to produce sanitized water. In the illustrated embodiment, sanitized water is stored in the boiler; although it is to be understood that a separate reservoir for sanitized water may be employed. As illustrated, the system includes a level probe 18 for controlling the water level in the boiler, and further includes a pressure switch 20 and a temperature switch 22 for regulating operation of the boiler.

Preferably, the boiler operates at 1.5 to 2.0 atmospheres of pressure, and is regulated by the pressure control switch 20. This assures that the water and steam produced by the boiler are at approximately 240° F., which will assure that the water delivered by the boiler is sanitized. The boiler is under constant pressure, which eliminates the need for a delivery pump or other secondary pressure regulation in the delivery lines.

The system includes a sanitized water delivery line 24 and a steam delivery line 26 in communication with the boiler. Both of these lines are in communication with a diverter valve 28 which, as illustrated, is a solenoid operated valve. The diverter valve 28 is also in communication with a fluid delivery line. The diverter valve allows for selectable connection of the steam line 26 or the sanitized water line 24 to the fluid delivery line 30.

When the system is in operation and the operator is rendering dental services to a patient, sanitized water is delivered from the fluid delivery line 30 to dental irrigators, dental drill handpieces and the like. When it is necessary to resanitize the system, the diverter valve 28 is operated so as to allow the fluid delivery line 30 to be purged with live steam. This flow of steam will remove all biofilm from the line and render the line sanitized. Additionally, the steam will clean workpieces such as irrigators, drill motors and the like.

Still other features of the invention are shown in FIG. 1. For example, dental workstations generally include a compressed air line 27 for powering dental drills, in combination with a water spray. The compressed air line is also coupled to a handpiece used to dry the worksite, remove debris and the like. Typically, compressed air used in dental situations is cold as a result of expansion in the delivery system. In the present invention, a heat exchanger 32 is included for the purpose of transferring excess heat from the sanitized water to the input compressed air. As illustrated, the heat exchanger 32 includes a primary tube in tube exchanger 31, as well as a secondary heat exchanger 33 which includes a fan 35 having a temperature regulator 37. In this manner, both the air and water are regulated to provide a comfortable temperature for the patient.

In most preferred embodiments, the boiler will be an electrically heated boiler. It has been found that boilers of the type employed in espresso machines, cappuccino makers and similar coffee brewing apparatus can be readily adapted to the present invention. Such boilers are capable of rapidly generating steam and hot water. They are fairly low in cost, compact and can be incorporated into conventional dental systems. One such boiler having utility in the present invention is available from Lamarzocco International of Seattle, Wash., under the designation WP/I. It is to be understood that other boilers may also be employed in the present invention. In general, the system is operated and configured so that the sanitized water reservoir is maintained at an elevated temperature so as to discourage any further microbial growth. Also, in those instances where the reservoir is integral with the boiler, reservoir size and water usage rates are selected so that fresh water input to the system for the purpose of replacing sanitized water drawn therefrom, does not unduly lower the temperature of the water in the reservoir so as to compromise sanitization.

Figure 2:
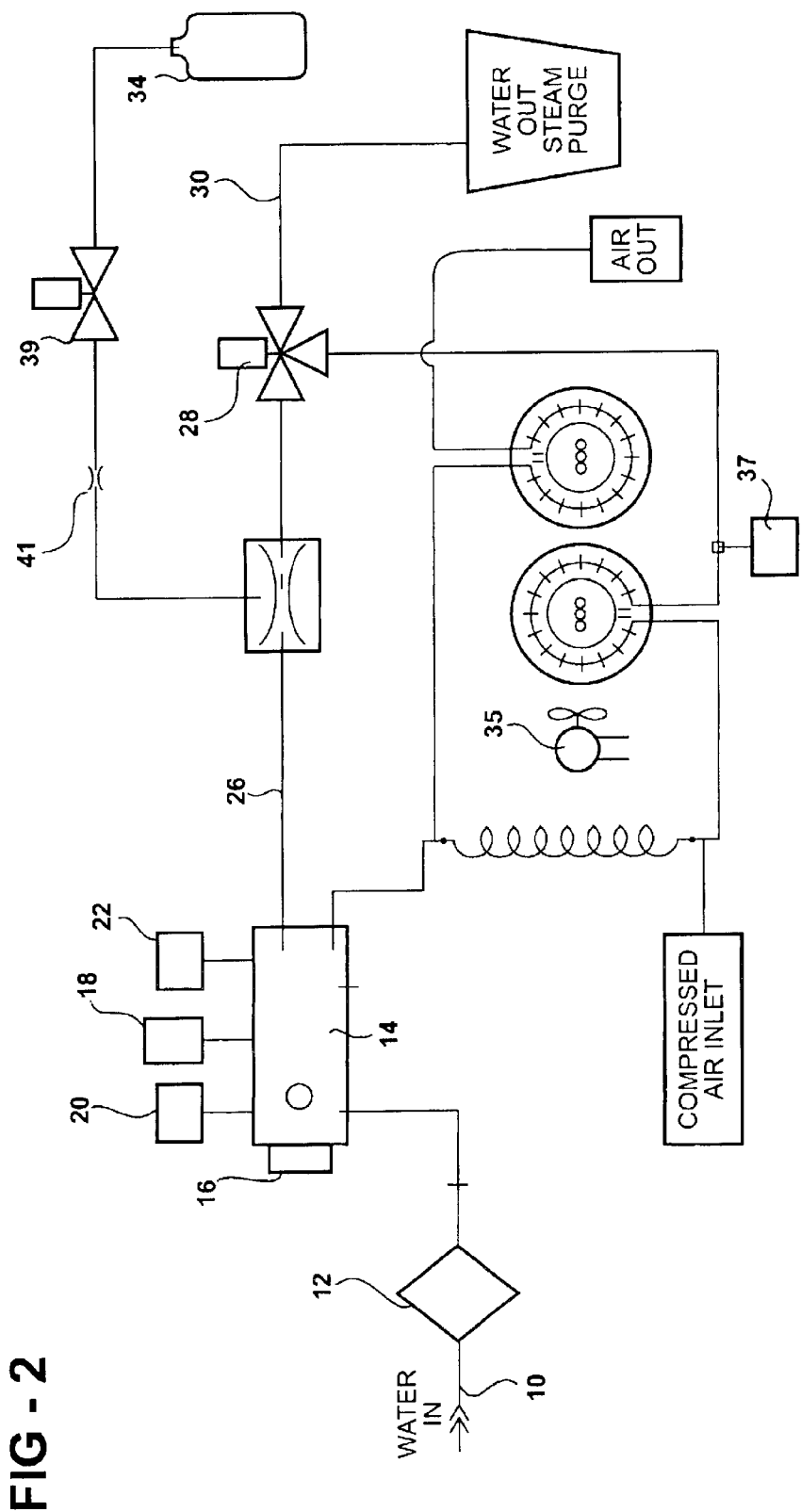
FIG. 2 is a schematic depiction of another embodiment of water line decontamination system of the present invention which includes a chemical agent delivery unit.

Referring now to FIG. 2, there is shown another embodiment of the present invention. The FIG. 2 embodiment is generally similar to the FIG. 1 embodiment, and like structures will be referred to by like reference numerals. The FIG. 2 embodiment differs from that of FIG. 1 in that it also includes a chemical dispenser unit therein. As shown in FIG. 2, the system is operative to deliver a material, such as a chemical biocide, surfactant, detergent, or the like into the fluid delivery line 30 of the system. The chemical agent is contained in a dispenser reservoir 34 which communicates with the steam delivery line 26 via a steam ejector 36. As is known in the art, a steam ejector operates on the venturi effect to draw material from the reservoir 34 into the steam delivery line 26. The system may include a shutoff valve 39 and a metering orifice 41 to control the flow of the chemical agent. A system of this type may be preferably employed in those instances where the system of the present invention is being retrofit onto equipment having very high levels of biofilm contamination. In such instance, the chemical agent may be employed for initial cleanings, after which steam cleaning will suffice.

Figure 3:
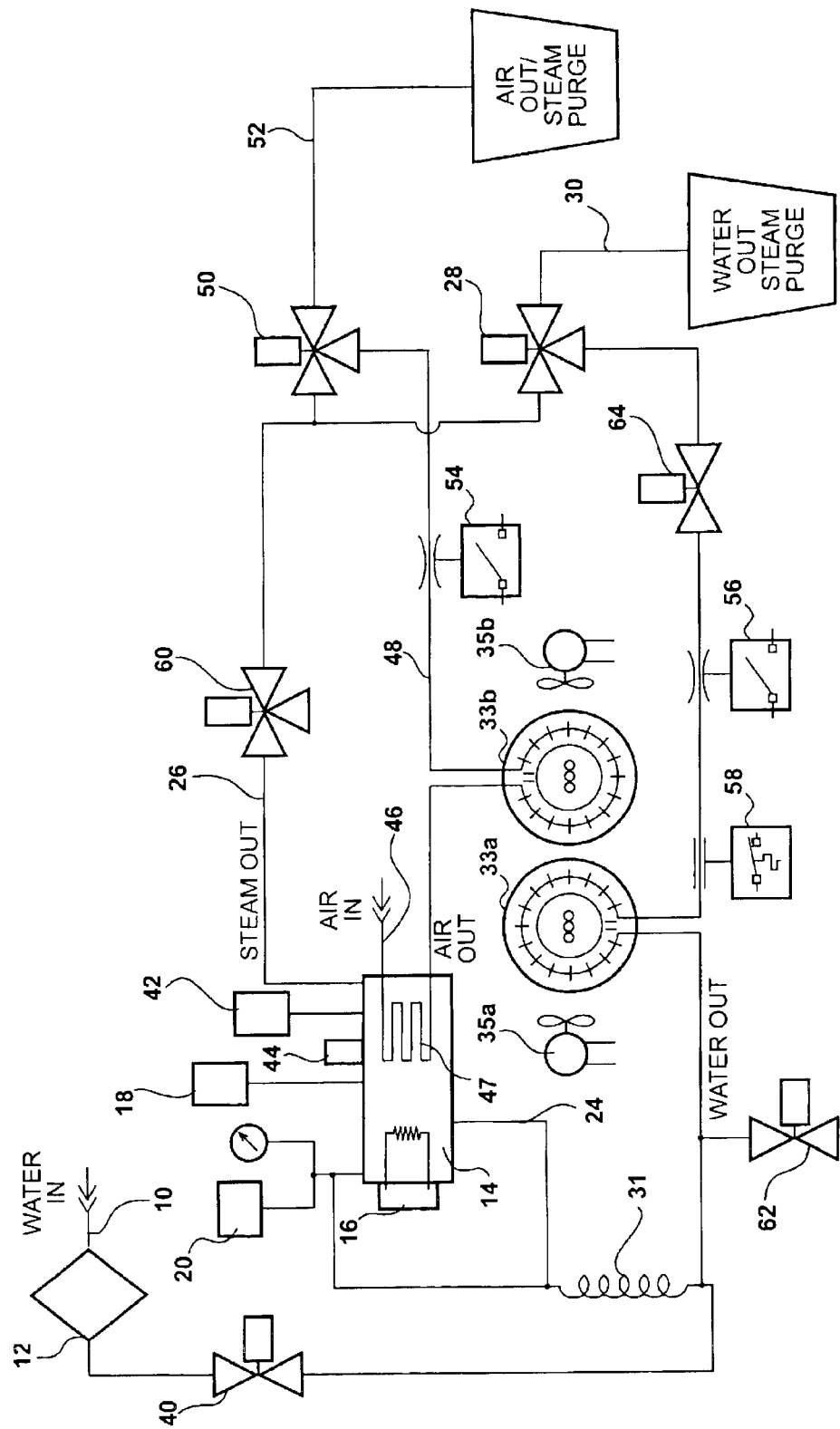
FIG. 3 is a schematic depiction of another embodiment of the present invention which operates to sanitize the air delivery line of a dental workstation.

Referring now to FIG. 3, there is shown another embodiment of the present invention which is configured for use with a dental unit workstation. The system of FIG. 3 is generally similar to the system of FIG. 1, and like structures will be referred to by like reference numerals; however, the system of FIG. 3 is further operative to sanitize a compressed air line of a dental workstation and to temperature control the air delivered thereby.

In the system of FIG. 3, water enters through a water inlet 10 which has a water softener and/or filter cartridge 12 associated therewith. Flow of inlet water may optionally be controlled by means of a solenoid 40, or by a valve or the like. In this embodiment, the input water is warmed in a tube in tube heat exchanger 31 which is also in fluid communication with the sanitized water outlet line 24 of the system. The input water enters the boiler 14 and is heated by the heater 16 to produce steam and sanitized water as discussed hereinabove. As further discussed with reference to the previous embodiments, the boiler has a pressure gauge and switch 20 and water level probe 18 associated therewith to control the operation of the boiler. As further shown in this embodiment, the system includes a pressure relief valve 42 to prevent accidental over pressurization of the boiler 14. The system may also include a vacuum relief valve 44. The vacuum relief valve 44 functions to relieve any vacuum which is created when the boiler is shut off and allowed to cool from its operating temperature. Cooling of the boiler will cause steam to condense thus creating a potential vacuum. Since the system has been designed for pressure operation, the vacuum could damage the boiler or other components of the system; or it could cause the suck-back of water through the delivery lines, if a pressure relief valve 44 is not included.

The FIG. 3 system also includes a compressed air input line 46 which can be placed in communication with an air compressor, compressed air tank or the like. Compressed air from the air input line 46 passes through a heat exchange coil 47 disposed within the boiler 14 and is warmed. The warmed air passes through an air delivery line 48 and through a heat exchanger 33b which includes a thermostatted fan 35b and which operates to temper the heated air to a patient-acceptable temperature. The temperature controlled air then passes through a diverter valve 50, which in this instance is a solenoid operated valve generally similar to the diverter valve 28 previously described. The steam output line 26 is also in communication with this diverter valve 50, and as will be appreciated, operation of the diverter valve 50 will selectably permit passage of either steam or tempered air therethrough to an air delivery line 52 which is in communication with the dental workstation. In this manner, the system may be employed to sanitize the air delivery portion of the dental unit.

The FIG. 3 system further includes a first flow switch 54 which is disposed in the air delivery line 48, and a second flow switch 56 which is disposed in the sanitized water delivery line 24. These flow switches 54, 56 operate to activate their respective fans 35a, 35b when air or water is flowing so as to provide temperature control. In this embodiment, the sanitized water line also includes a temperature responsive switch 58 which halts the flow of water if the temperature is outside of a predetermined range. As further illustrated, a steam control solenoid valve 60 is disposed in the steam delivery line. This provides backup control of steam delivery and increases the safety level of the system. The FIG. 3 embodiment also includes a manually operated drain valve 62 disposed in the sanitized water output line. This valve facilitates draining and cleaning of the boiler. Another solenoid control valve 64 is disposed in the sanitized water line 24, and provides backup control of water delivery.

Yet other modifications and variations of the FIG. 3 system may be implemented. For example, the system may further include the chemical agent dispenser of the FIG. 2 embodiment. Also, the system may be further reconfigured to allow for steam sanitization of yet other lines and equipment.

Figure 4:
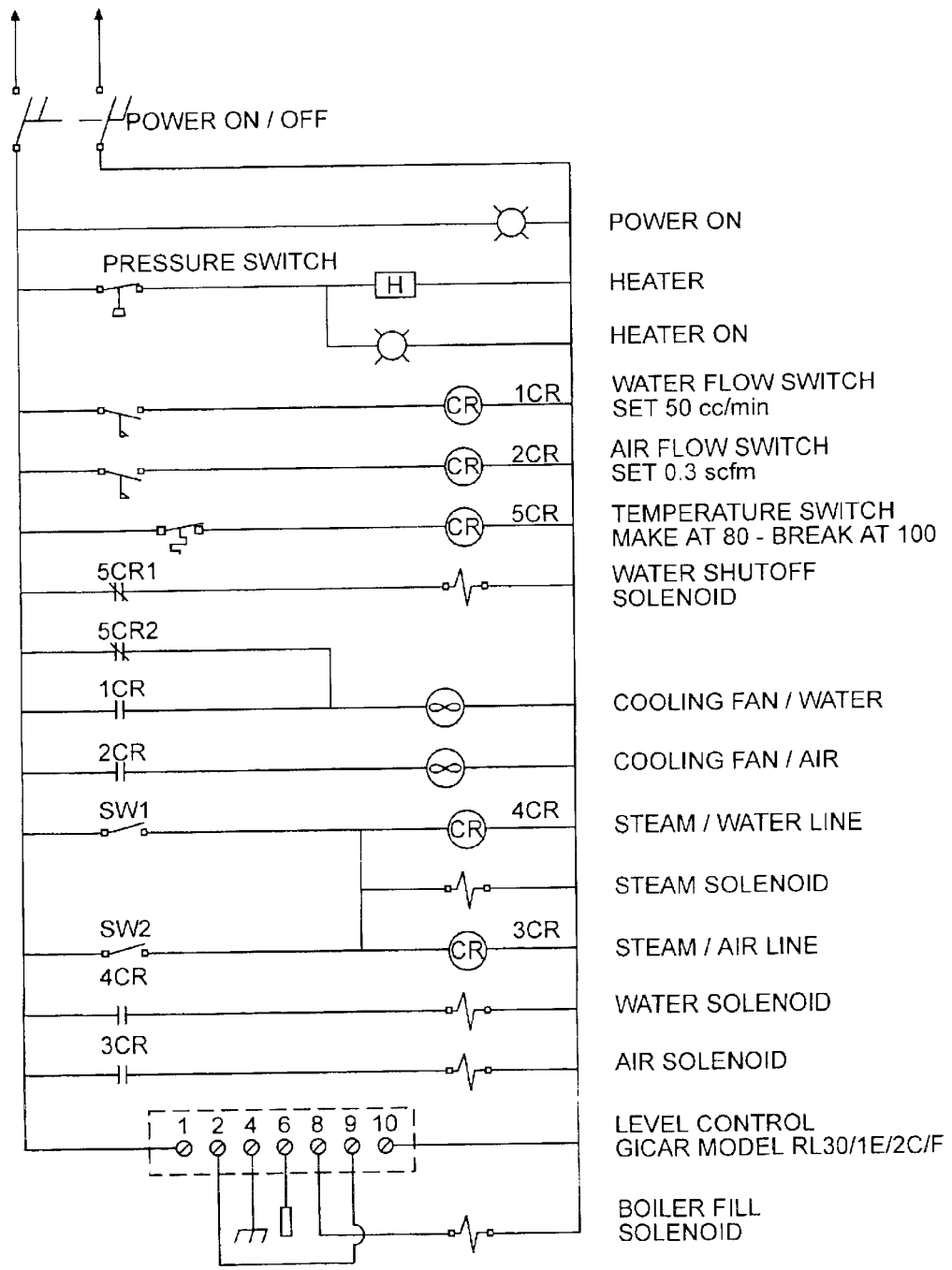
FIG. 4 is a schematic depiction of the electrical system of the FIG. 3 unit.

FIG. 4 is a schematic depiction of the electrical control system of the FIG. 3 embodiment.

It is to be understood that yet other modifications and variations of the present invention may be implemented in view of the teaching presented herein. All of such embodiments are within the scope of the present invention. Also, while the invention has been described with specific reference to a dental system, it is to be understood that systems of this type may be employed for other medical related purposes as well as for food service uses and industrial applications. For example, the systems of the present invention may be incorporated into dialysis units, medical irrigators, beverage dispenser systems, water coolers, food preparation equipment, semiconductor processing lines, machine tools and the like. Also, the systems of the present invention can be employed to clean oil lines, fuel lines and other such industrial equipment wherein biofilm buildup is a problem.

The foregoing drawings, discussion and description are illustrative of specific embodiments of this invention, but are not meant to be limitations to the practice thereof. It is the following claims, including all equivalents thereof, which define the scope of the invention.

What is claimed is:

1. A self-cleaning system for delivering sanitized water or steam to a dental workstation, said system comprising:

a water inlet which is connectable to a source of water;

a boiler in fluid communication with the water inlet, the boiler being operable to provide steam and heat-sanitized water;

a sanitized water delivery line in fluid communication with the boiler;

a steam delivery line in fluid communication with the boiler;

a fluid delivery line which is connectable to the dental workstation; and a diverter valve in fluid communication with the sanitized water delivery line, the steam delivery line, and the fluid delivery line; said diverter valve being operable to selectively establish fluid communication between the fluid delivery line and the steam delivery line, or the fluid delivery line and the sanitized water delivery line; whereby said fluid delivery line may be used to selectively deliver sanitized water to the dental workstation, or to deliver steam to said dental workstation, whereby said steam may be employed to sanitize said fluid delivery line and said dental workstation.

2. The system of claim 1, further including a heat exchanger, said heat exchanger being operable to cool the heat sanitized water provided by said boiler.

3. The system of claim 2, wherein said heat exchanger is further operable to transfer heat from said heat sanitized water to a flow of water passing through said water inlet.

4. The system of claim 2, wherein said heat exchanger is further operable to transfer heat from said heat sanitized water to a stream of air so as to heat said air.

5. The system of claim 1, further including a sanitized water reservoir in fluid communication with said boiler and with said sanitized water delivery line, said reservoir being operable to store sanitized water therein.

6. The system of claim 1, wherein said boiler is operable to provide steam at a pressure greater than atmospheric pressure.

7. The system of claim 6, wherein said steam pressure is employed to deliver said heat sanitized water from said boiler to said sanitized water delivery line, through said diverter valve, and through said fluid delivery line without the assistance of a mechanical pump.

8. The system of claim 1, wherein said boiler further includes a pressure relief valve.

9. The system of claim 6, wherein said boiler operates at a pressure in the range of 1.5–2.0 atmospheres.

10. The system of claim 1, wherein said boiler is operable to provide heat sanitized water at a temperature in the range of 220–240° F.

11. The system of claim 1, further including a temperature controller in communication with the boiler, said temperature controller being operable to maintain the water in the boiler at a preselected temperature.

12. The system of claim 1, further including a pressure controller in communication with the boiler, said pressure controller being operable to maintain the steam in the boiler at a preselected pressure.

13. The system of claim 1, further including a water conditioner in fluid communication with the water inlet.

14. The system of claim 13, wherein said water conditioner includes a water softener cartridge.

15. The system of claim 13, wherein said water conditioner includes a water filter.

16. The system of claim 1, wherein said boiler is electrically heated.

17. The system of claim 1, wherein said boiler further includes a drain line in fluid communication therewith, said drain line being separate from said sanitized water delivery line.

18. The system of claim 1, further including a chemical agent reservoir in fluid communication with the fluid delivery line, said reservoir being operable to introduce a chemical composition into the fluid delivery line.

19. The system of claim 18, further including a steam ejector in fluid communication with the steam delivery line and the chemical agent reservoir, said steam ejector being operable to deliver said chemical composition into the fluid delivery line when the diverter valve is actuated so as to establish fluid communication between the steam delivery line and the fluid delivery line.

20. A system for selectably delivering sanitized water or steam to a workstation, said system comprising:

a water inlet which is connectable to a source of water;

a boiler in fluid communication with the water inlet, said boiler being operable to provide steam and heat sanitized water;

a sanitized water delivery line in fluid communication with the reservoir;

a steam delivery line in fluid communication with the boiler;

a fluid delivery line; and a diverter valve in fluid communication with the sanitized water delivery line, the steam delivery line, and the fluid delivery line; said diverter valve being operable to selectively establish fluid communication between the fluid delivery line and the steam delivery line, or the fluid delivery line and the sanitized water delivery line; whereby said fluid delivery line may be used to deliver sanitized water to the workstation or said steam may be employed to sanitize said fluid delivery line.

21. A method for delivering sanitized water to, and cleaning biofilm from, a fluid delivery line, said method comprising:

A. providing a fluid delivery system comprising:
   a water inlet which is connectable to a source of water;
   a boiler in fluid communication with the water inlet, the boiler being operable to provide steam and heat sanitized water;
   a sanitized water delivery line in fluid communication with the reservoir;
   a steam delivery line in fluid communication with the boiler; and
   a diverter valve in fluid communication with the sanitized water delivery line, the steam, delivery line, and with the fluid delivery line;
   said diverter valve being operable to selectively establish fluid communication between the fluid delivery line and the steam delivery line or the fluid delivery line and the sanitized water delivery line;

B. introducing water into said boiler through said water inlet;

C. operating said boiler so as to generate steam and heat sanitized water; and

D. selectably operating said diverter valve so as to deliver heat sanitized water from said boiler to said fluid delivery line, or to deliver steam from said boiler to said fluid delivery line whereby said steam functions to remove biofilm from said fluid delivery line.

* * * * *